United States Patent [19]
Simpkins et al.

[11] Patent Number: 5,972,923
[45] Date of Patent: Oct. 26, 1999

[54] METHODS AND COMPOSITIONS TO ENHANCE THE CYTOPROTECTIVE EFFECTS OF POLYCYCLIC PHENOLIC COMPOUNDS THROUGH THE SYNERGISTIC INTERACTION WITH ANTI-OXIDANTS

[75] Inventors: James W. Simpkins; Kelly E. Gridley; Pattie S. Green, all of Gainesville, Fla.

[73] Assignee: University of Florida Research Foundation, Inc., Gainesville, Fla.

[21] Appl. No.: 09/007,915

[22] Filed: Jan. 16, 1998

Related U.S. Application Data

[60] Provisional application No. 60/058,104, Sep. 5, 1997, provisional application No. 60/053,516, Jul. 23, 1997, and provisional application No. 60/035,537, Jan. 16, 1997.

[51] Int. Cl.[6] .......................... A61K 31/56; A61K 38/00; A61K 31/355; A61K 33/04
[52] U.S. Cl. .............................. 514/182; 514/2; 514/458; 424/702
[58] Field of Search ................................ 514/2, 182, 458; 424/702

[56] References Cited

FOREIGN PATENT DOCUMENTS

WO 96/10401  4/1996  WIPO .

OTHER PUBLICATIONS

Ayres, Stacey, et al., "Estradiol–17β as an antioxidant: Some distinct features when compared with common fat–soluble antioxidants", *J. Lab Clin Med*, vol. 128, No. 4, Oct. 1996, pp.367–375.

Capel. Ifor D., et al. "The Effect of Prolonged Oral Contraceptive Steroid Use on Erythrocyte Glutathione Peroxidase Activity", *Journal of Steroid Biochemistry*, vol. 14, 1981, pp. 729–732.

Lacort, Mercedes, et al., "Protective Effect of Estrogens and Catecholestrogens Against Peroxidative Membrane Damage in vitro", *Lipids*, vol. 30, No. 1, 1995, pp. 141–146.

Massafra, Cosimo, et al., "Antioxidant Erythrocyte Enzyme Activities During Oral Contraception", *Contraception*, vol. 47, 1993, pp. 591–596.

Mooradian, Arshag D., "Antioxidant Properties of Steroids", *J. Steroid Biochem. Molec. Biol.*, vol. 45, No. 6, 1993, pp. 509–511.

Ruiz–Larrea, Begona, et al. "Effects of Estrogens on the Redox Chemistry of Iron: A possible mechanism of antioxidant action of estrogens", *Steroids*, vol. 60. Nov. 1995, pp. 780–783.

Wander, Rosemary C., et al., "Effects of interaction of RRR–α–Tocopheryl acetate and fish oil on low–density–lipoprotein oxidation in postmenopausal women with and without hormone–replacement therapy", *American Journal of Clinical Nutrition*, vol. 63, 1996, pp. 184–193.

*Primary Examiner*—Raymond Henley, III
*Attorney, Agent, or Firm*—Bromberg & Sunstein LLP

[57] ABSTRACT

The present invention concerns methods and compositions for enhancing the cytoprotective effects of polycyclic phenolic compounds through the synergistic interaction with anti-oxidants.

26 Claims, 7 Drawing Sheets

METHODS AND COMPOSITIONS TO ENHANCE THE CYTOPROTECTIVE EFFECTS OF POLYCYCLIC PHENOLIC COMPOUNDS THROUGH THE SYNERGISTIC INTERACTION WITH ANTI-OXIDANTS

CROSS REFERENCE

This application claims benefit of the earlier filing date of U.S. provisional patent applications, Ser. No. 60/058,104 dated Sep. 5, 1997, Ser. No. 60/053,516 dated Jul. 23, 1997 and Ser. No. 601035,537 dated Jan. 16, 1997, these provisional applications are incorporated herein by reference.

BACKGROUND

There is a need for treatments that protect cells from cell death resulting from episodes of disease, trauma, isolation and removal of tissues or cells from the body, or exposure to toxins. This need extends to treatments for nerve cell loss associated with chronic or acute neurodegenerative disorders or trauma; treatments to minimize tissue damage resulting from ischemia where ischemia may occur as a result of stroke, heart disease, a transplantation event, or other event resulting in a cut-off in nutritional supply to tissues; and treatment to modulate cell death associated with conditions such as osteoporosis or anemia. The absence of an effective cytoprotective therapy can result in either loss of life or a general decline in the quality of life including permanent disability with high health care costs to patients, their families and the health care providers. One approach to minimize pathologic changes has been to attempt to neutralize the oxidative stress that is associated with an accumulation of free radicals in the extracellular space. Mooradian, J. Steroid Biochem. Molec. Biol. 45 (1993) 509–511 has reported that certain estrogens have significant anti-oxidant properties in in vitro biochemical assays but this effect is not seen with all estrogens. Because of the variation in anti-oxidant properties noted by Mooradian in his biochemical assays, he concluded that steroid molecules must have certain anti-oxidant determinants which were as yet unknown. Similar observations concerning steroids with phenolic A rings were reported in WO 95/13076 using biochemical assays to show anti-oxidant activity. The assays used by Mooradian and by WO 95/13076 were biochemical assays and as such did not directly examine the effects on cells of these molecules. U.S. Pat. No. 5,554,601 (1996) however described cell based assays to determine a method of conferring neuroprotection on a population of cells using estrogen compounds based on demonstrated cell protective effects.

Oxidative damage has been associated with a variety of neurodegenerative diseases including Alzheimer's disease (AD); and the aging process. (Benzi et al. Free Radic. Biol. Med. 19, (1995); 77–101, and U.S. Pat. No. 5,554,601 incorporated herein by reference) . Cell death also occurs following an ischemic event in the body resulting from nutrient deprivation which may be associated with oxygen deprivation resulting from an occlusion in a cerebrovascular or cardiovascular location or may be associated with trauma or disease.

There is a need for improved methods of protecting both men and women from the consequences of abnormal cell death in body tissues.

SUMMARY

In an embodiment of the invention, a method is provided for conferring cytoprotection on a population of cells that includes providing a polycyclic phenol compound, and an anti-oxidant compound; and administering the polycyclic phenol compound and the anti-oxidant compound to the population of cells at an effective dose so as to confer cytoprotection such that the combined cytoprotective effect of the polycyclic phenolic compound and the anti-oxidant compound is greater than the additive effect of each compound administered separately under otherwise similar conditions.

A further embodiment of the invention is a method of conferring cytoprotection on a population of cells in a subject, including the steps of providing a combination therapeutic dose containing an anti-oxidant and a polycyclic phenolic compound in a pharmaceutical formulation; administering the formulation in an effective dose to the population of cells such that the cytoprotective effect of the combination in the subject is greater than the additive effect of each compound provided separately; and protecting cells in the subject that would otherwise deteriorate and die in the absence of the pharmaceutical formulation.

In further embodiments of the invention, the combined effect may be a 100–10,000 fold enhancement, more particularly a 100–5,000 fold enhancement, more particularly a 1,000–5,000 fold enhancement of cytoprotection resulting from the combined effect of the polycyclic compound and the anti-oxidant compared with each compound separately. In further embodiments of the invention, the polycyclic phenol compound is an estrogen compound more particularly an estrogen compound having insubstantial sex activity exemplified by the (x isomer of estradiol. In certainembodiments of the invention, the anti-oxidant is selected from the group consisting of a thiol, a phenol, a spin trapping agent, an aromatic amine, a carotenoid, a flavonoid, a selenium, an aminosteroids and an ubiquinones. In a further embodiment of the invention, cytoprotection includes neuroprotection.

BRIEF DESCRIPTION OF THE FIGURES

| with GSH (3.25 μM) | without GSH |
|---|---|
| —○— 17β-estradiol | —●— 17β-estradiol |
| —△— α-estradiol | —▲— α-estradiol |
| —□— E-3-ol | —■— E-3-ol |

DETAILED DESCRIPTION

A preferred embodiment of the invention is directed to the novel finding that the cytoprotective effect of polycyclic phenol compounds is substantially enhanced when administered with at least one additional anti-oxidant compound.

The term "cytoprotection" is defined here and in the claims as the protection of cells against cell death or cell damage that would otherwise occur in the absence of a protective agent, where the cell death or cell damage might be caused by any mechanical damage, nutritional deprivation including oxygen deprivation, trauma, disease processes, damage due to exposure to chemicals or temperature extremes, aging or other cause.

The term "estrogen compound" as used here and in the claims is defined as any of the structures described in the 11th Edition of "Steroids" from Steraloids Inc., Wilton N.H., here incorporated by reference. Included in this definition are isomers and enantiomers including non-steroidal estrogens formed by modification or substitution of the compounds in the Steraloid reference. Other estrogen compounds included in this definition are estrogen derivatives, estrogen metabolites and estrogen precursors as well as those molecules capable of binding cell associated estrogen receptor as well as other molecules where the result of binding specifically triggers a characterized estrogen effect. Also included are mixtures of more than one estrogen, where examples of such mixtures are provided in Table II below. Examples of α estrogen structures having utility either alone or in combination with other agents are provided in FIG. 9.

The terms "17-E2, β-estradiol, 17β-estradiol, β-17-E2, 17β-E2, E2, 17βE2, βE2" as used here and in the claims are intended to be synonymous. Similarly, the terms "α17-E2, α-17-E2 , α-estradiol 17 α-estradiol, 17αE2, αE2" as used here and in the claims are intended to be synonymous and correspond to the a isomer of 17β-estradiol.

The abbreviation "E-3-ol" as used here and in the claims represents estratriene-3-ol The terms "polycyclic phenolic compound, polycyclic compounds or polycyclic phenols" as used here and in the claims are meant to be synonymous and are defined according to patent application Ser. No. 08/685,574 herein incorporated by reference and includes any compound having a phenolic A ring as defined below and may contain up to 3 additional ring structures exemplified by the following:

(a) Cyclopentanophen (A) anthrene ring compounds having two, three or four rings and a hydroxyl group on carbons 1, 2, 3 and/or 4 of the A ring. Additionally, R groups selected from sodium, potassium and/or ammonium salts may be attached to the alpha or beta positions to replace hydrogen on any available carbon in the structure. Such compounds may be further substituted on the A ring so as to preserve a single-OH group and further form a pyridine, pyriazine, pyrimidine, s-triazine, v-triazne, or as-triazine.

(b) The phenol A ring with possible additional substitutions listed above may further be linked to a six carbon ring having one or more of the following structures-benzene, cyclohexane, 1, 2-pyran; 1, 4-Pyran, 1, 2-pyrone, 1, 4-pyrone; 1, 2-Dioxin; 1, 3-Dioxin (dihydro form) pyridine; pyridazine; pyrimidine; pyrazine; piperazine; s-triazine; as triazine, v-triazine, 1, 2, 4-Oxazine; 1, 3, 2-Oxazine; 1, 3, 6-Oxazine (Pentoxazole); 1, 2, 6 Oxazine; p-Isoxazine; 1, 2, 5-Oxathiazine; 1, 2, 6-Oxathiazine; 1, 4, 2-Oxadiazine, 1, 3, 5, 2-Oxadiazine; morpholine (tetrahydro-p-isoxazine). Any six ringed structure listed above may be linked to any of the following 5 ring structures: Furan; Thiphene (Thiofuran); pyrrole (Azole); isopyrrole (isoazole); 3-isopyrrole (isoazole); Pyrazole (1, 2-Daizole); 2-isoimidazole (1, 3-isodiazole); 1, 2, 3-triazle; 1, 2, 4 triazole; 1, 2-diothiole; 1, 2, 3-oxathiole, isoxazole (furo(a) monozole); oxazole (furo(b) monozole); thiazole; isothiazole; 1, 2, 3-oxadiazole; 1, 2, 3, 4-oxatiazole; 1, 2, 3, 5-oxatriazole; 1, 2, 3-dioxazole; 1, 2, 4-dioxazole; 1, 3, 2-diaxazole; 1, 3, 4-dioxazole; 1, 2, 5-oxathiazole; 1, 3-oxathiole, cyclopentane.

(c) Any compound listed above where the cyclopentanophen (a) anthrene ring compound is selected from the group consisting of 1, 3, 5 (10), 6, 8-estrapentaen; 1, 3, 5 (10), 6, 8, 11-estrapentaen; 1, 3, 5 (10), 6,-estratetraen 1, 3, 5 (10), 7-estratetraen ; 1, 3, 5 (10) 8-estratetraen; 1, 3, 5 (10) 16-estratetraen; 1, 3, 5 (10) 15-estratetraen; 1, 3, 5 (10)-estratrien; 1, 3, 5 (10) 15-estratrien.

The term "anti-oxidant" as defined here and in the claims refers to any molecule that prevents oxidation of a particular substrate by a second molecule. Although not limiting, examples of anti-oxidants included in the invention are the following:

Thiols including glutathione, taurine, cystein, homocysteine, and α-lipoic acid; phenols: including probucol, salicylates, Trolox C, 3,4-dihydroxytoluene, 3, 4-dihydroxycinnamic acid, nordihydroxyquaiarectic acid, 2", 4'-dihydroxyacetophenone, 2', 5'-dihydroxyacetophenone, 3'4'-dihydroxyacetophenone, propylgallate; spin trapping agents including dimethyl-1-pyrroline-N-oxide, N-tert-butyl-α-phenylnitrone; aromatic amines including promethazine, chlorpromazine, ethoxquin, allopurinol, uric acid; carotenoids including β-carotene, α-carotene, γ-carotene, lypcopene, Caratol; flavonoids including (+)-catechin, dihydroquercetin, hesperetin, texasin, biochanin A, kaempferol, quercetin, and 6,7-dhydroxy-4'-methoxy-isoflavanol; selenium aminosteroids including trilazad mesylate, methyl prednisolone, suleptnate, lazaroids; and ubiquinones such as coenzyme Q2, coenzyme Q10. This list shall not be limiting.

Polycyclic Compounds Having a Terminal Phenolic A Ring in Combination with Anti-oxidants for Enhancing Cytoprotective Potency in a Synergistic Manner.

We have shown for the first time that an anti-oxidant in the extracellular milieu provides enhanced cytoprotection when administered to a subject together with a polycyclic compound having a phenolic A ring, such as estrogen, at physiologically and pharmacologically relevant doses. The enhanced effect of the combination of polycyclic phenolic compounds and anti-oxidants, more particularly compounds having insubstantial sex activity in combination with anti-oxidant thiols, more particularly estrogen compounds having insubstantial sex activity and glutathione, occurs to promote cell protection beyond that observed with any single compound. The combination of anti-oxidant and polycyclic phenolic compounds including estrogens has utility in protecting cells from damage resulting from any of a number of events that are known to be detrimental to the cell including chemical damage such as caused by free radicals, excitatory aminoacids and amyloid plaque. For example, the above combination is more effective for neuroprotection than either anti-oxidant or polycyclic phenolic compound alone and therefore presents a novel therapeutic approach to treating neuron loss in human subjects that occurs in neurodegenerative diseases such as Alzheimer's disease. In addition the combination therapy disclosed here has utility in treating other disease conditions which result from enhanced cell death including ischemia, trauma and aging.

The above observations are a surprising and unexpected extension on earlier observations made by us in which we identified the application of polycyclic phenolic compounds having a phenolic A ring for cell protection. Previously, we showed that polycyclic phenol compounds could protect against: neurodegeneration (U.S. Ser. No. 08/685,574 herein incorporated by reference); cell death associated with ischemia (U.S. Ser. No. 08/749,703 incorporated herein by reference); osteoporosis (Ser. No. 08/318,042, herein incorporated by reference); and cell death in tissues during tissue removal from the body and transplantation. (U.S. Ser. No. 08/782,883 incorporated herein by reference).

Figure 1A:
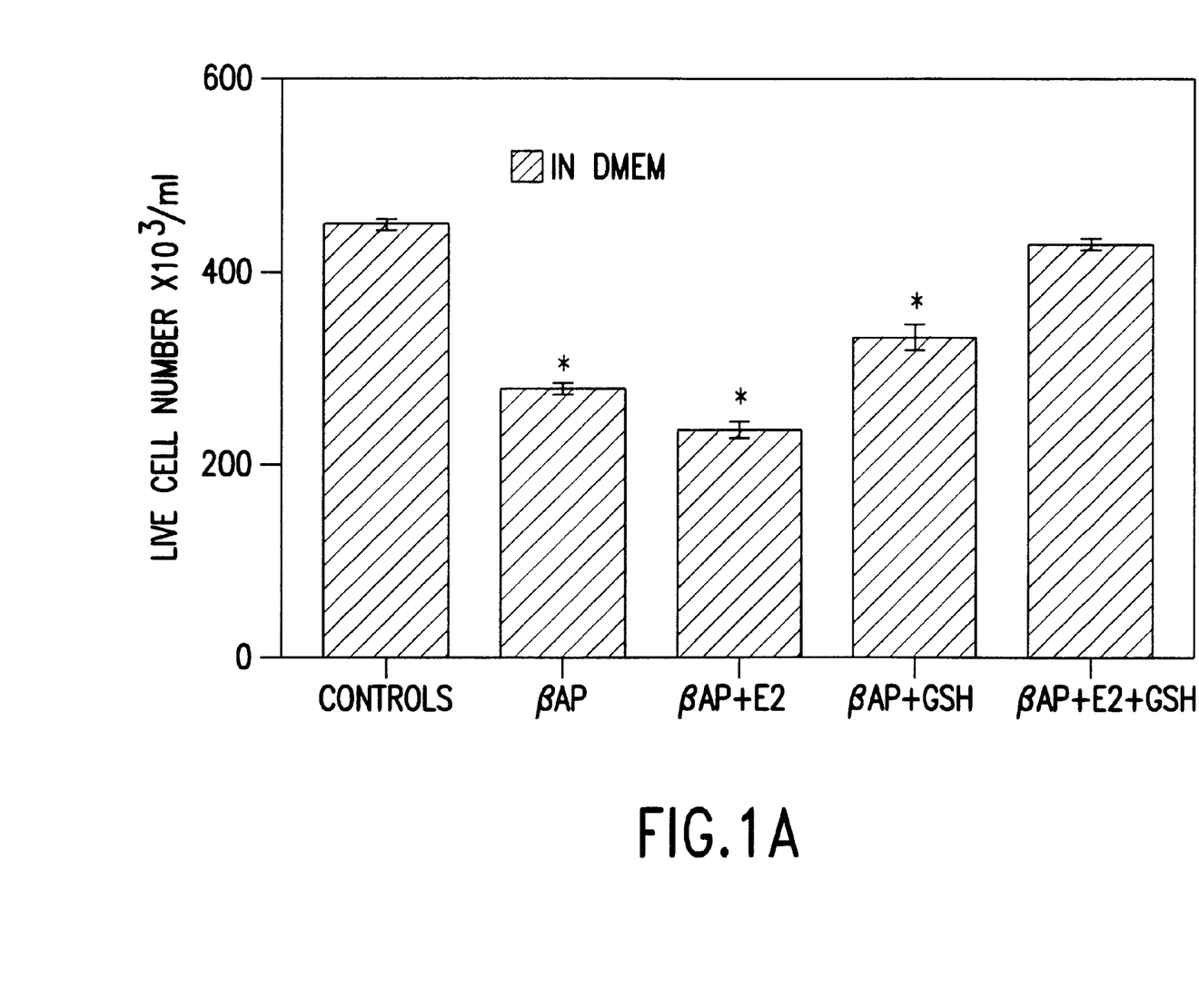
FIG. 1 shows the effect of glutathione (GSH) and 17β-estradiol on neuronal cells (SK-N-SH cells) treated with neurotoxic β-amyloid protein (βAP) where βAP is a peptide of 10 amino acids (amino acids 25–35), hereafter referred to as "βAP 25–35". The effects of 17β-estradiol (2 nM) and GSH (3.25 $\mu$M) on the toxicity induced by βAP 25–35 (20 $\mu$M) on SK-N-SH cells ($10^6$ cells/ml) in different cell culture media lacking GSH in the cell culture recipe is shown. Cells were plated at $10^6$ cells/ml and were exposed to vehicle, βAP 25–35, 17β-estradiol, GSH, or a combination as indicated. Controls represent the mean value for the vehicle, GSH, 17β-estradiol and GSH+17β-estradiol groups; were pooled together after it was determined they were not statistically significant from each other. Depicted are the mean values±SEM for 4–5 wells/group. *p<0.05 versus controls determined by ANOVA followed by Scheffe's post hoc test.
Figure 1B:
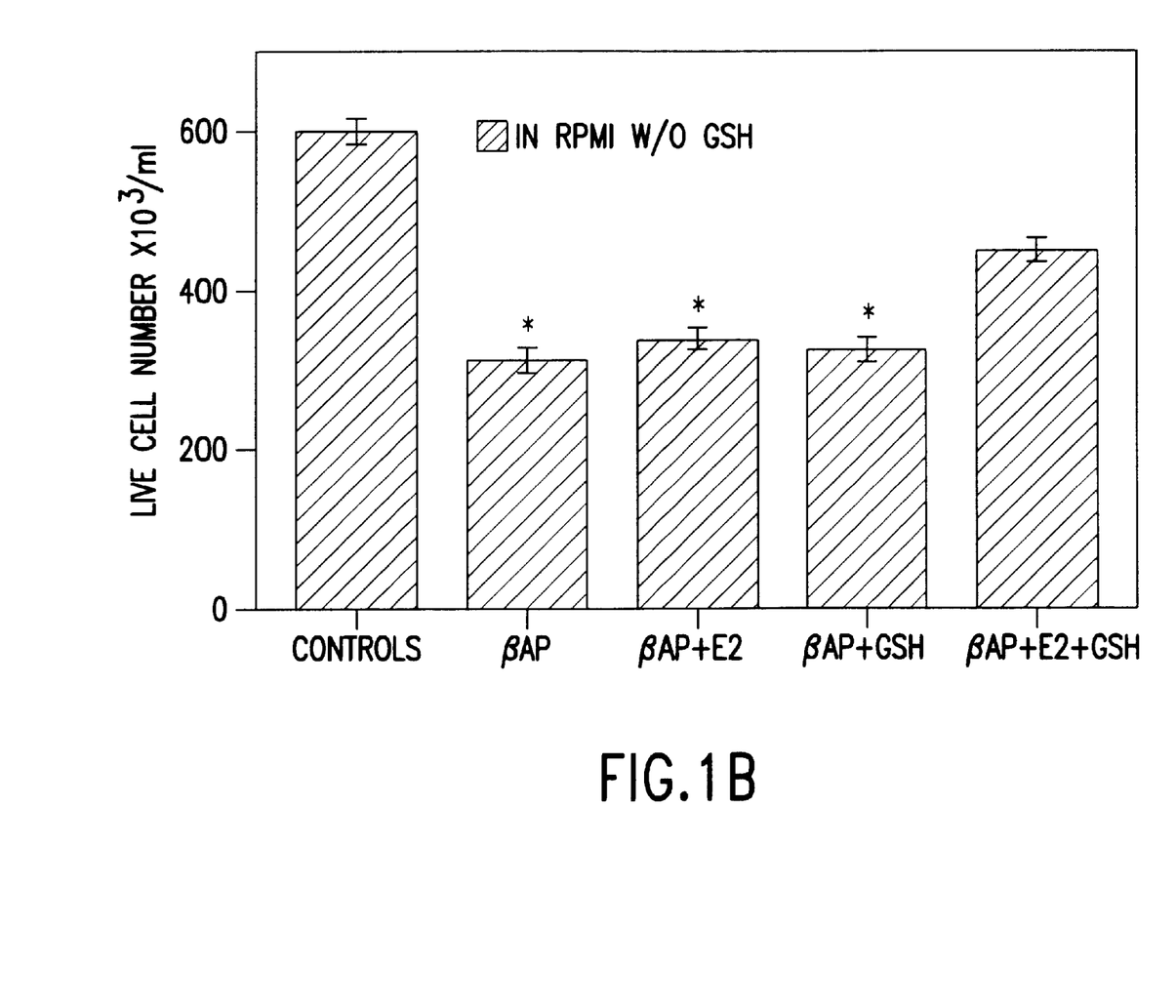
Figure 2:
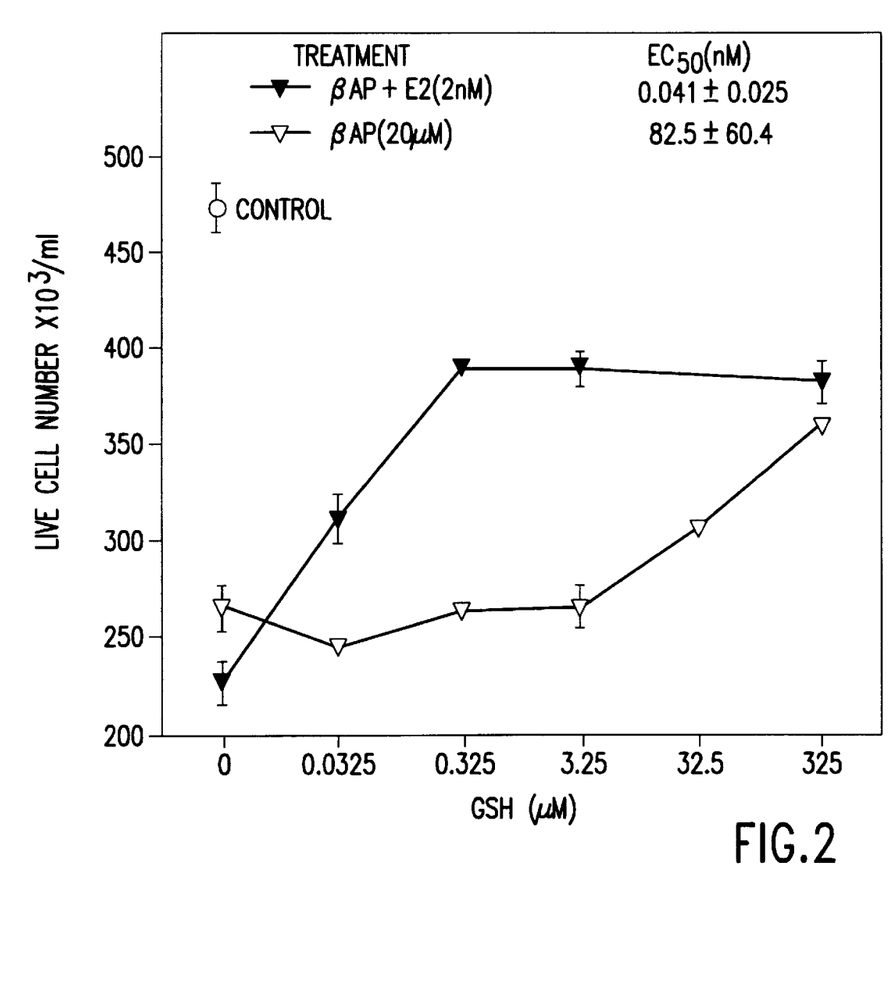
FIG. 2 shows the effect of GSH and 17β-estradiol on live SK-N-SH cell number treated with neurotoxic βAP 25–35 in the presence or absence of a non-protective dose of 17β-estradiol (2 nM). Cells were plated at $10^6$ cell/ml. The effect of varying concentrations of GSH in the presence of 17β-estradiol (filled triangles) were compared with cells treated with GSH in the absence of 17β-estradiol (open triangles). Depicted are the mean values±SEM for 6 wells per group. The effect of 17β-estradiol on the response to GSH was highly significant (F=41.48; p<0.001). A comparison of the $EC_{50}$ values for the different dose response curves using the Mann-Whitney Rank Sum Test showed a p=0.036 where the $EC_{50}$ for βAP25–35+17β-estradiol (2 nM) was 0.041±0.025 and for βAP 25–35 (20 μM) was 82.5±60.4.
Figure 4:
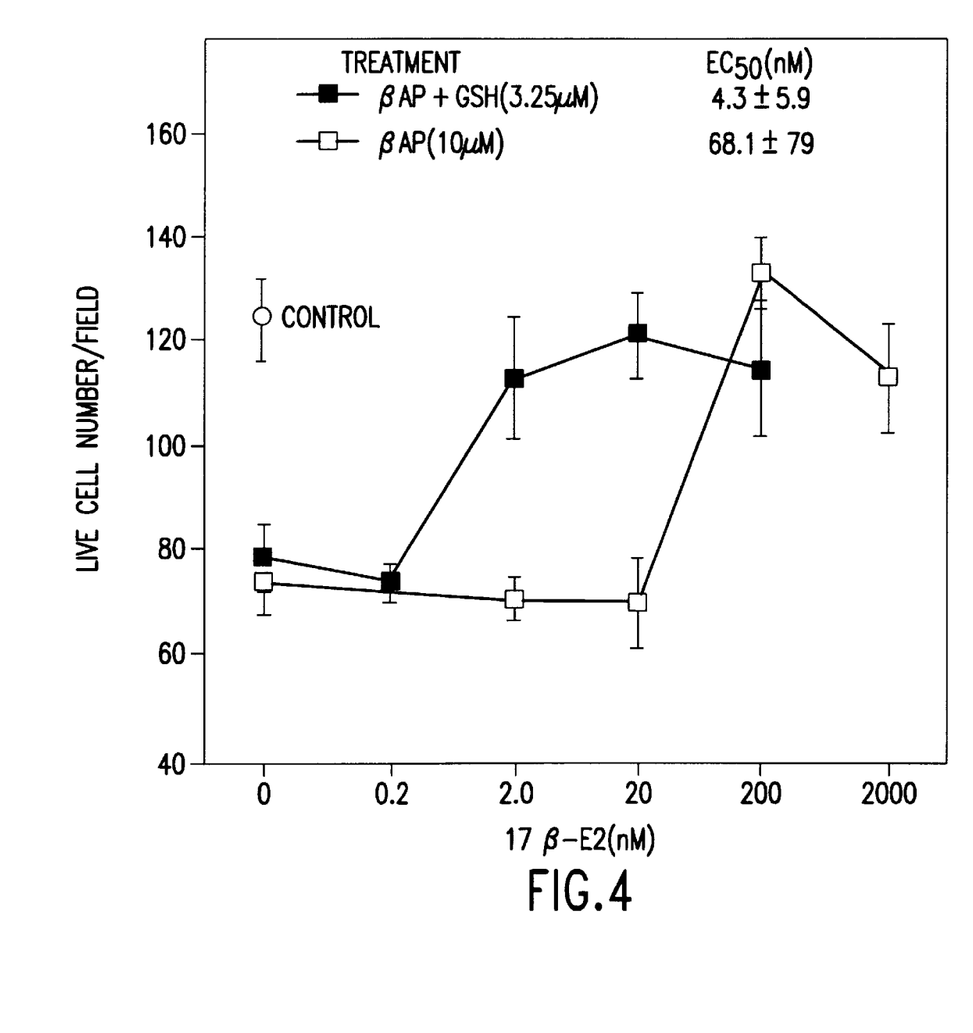
FIG. 4 shows the effects of dose of 17β-estradiol on the average number of rat primary cortical neurons per photographic field when subjected to a βAP 25–35 challenge in the presence and absence of a non-protective dose of GSH. Cells were plated and exposed to treatments as previously indicated at the doses noted. Depicted are the mean values±SEM for 4–7 wells per group. The effect of GSH on the response to 17β-estradiol was highly significant (F=8.53; p<0.005). A comparison of the $EC_{50}$ values for the different dose response curves using the Mann-Whitney Rank Sum Test showed a p<0.057.
Figure 5:
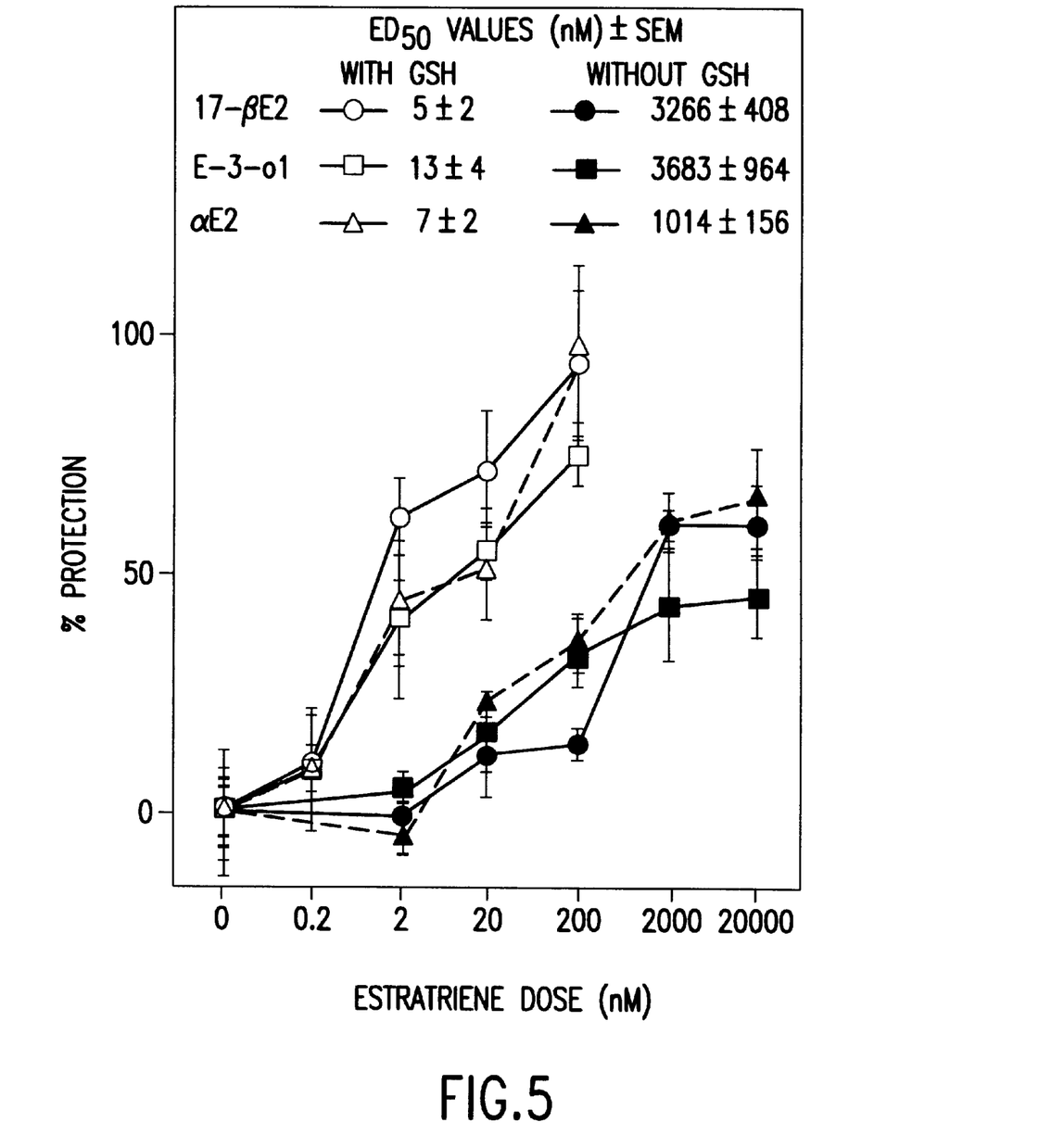
FIG. 5 shows the effects of estratrienes in the presence and absence of GSH on the neurotoxicity induced by βAP (25–35) in HT22 cells. The symbols represent.
Figure 6:
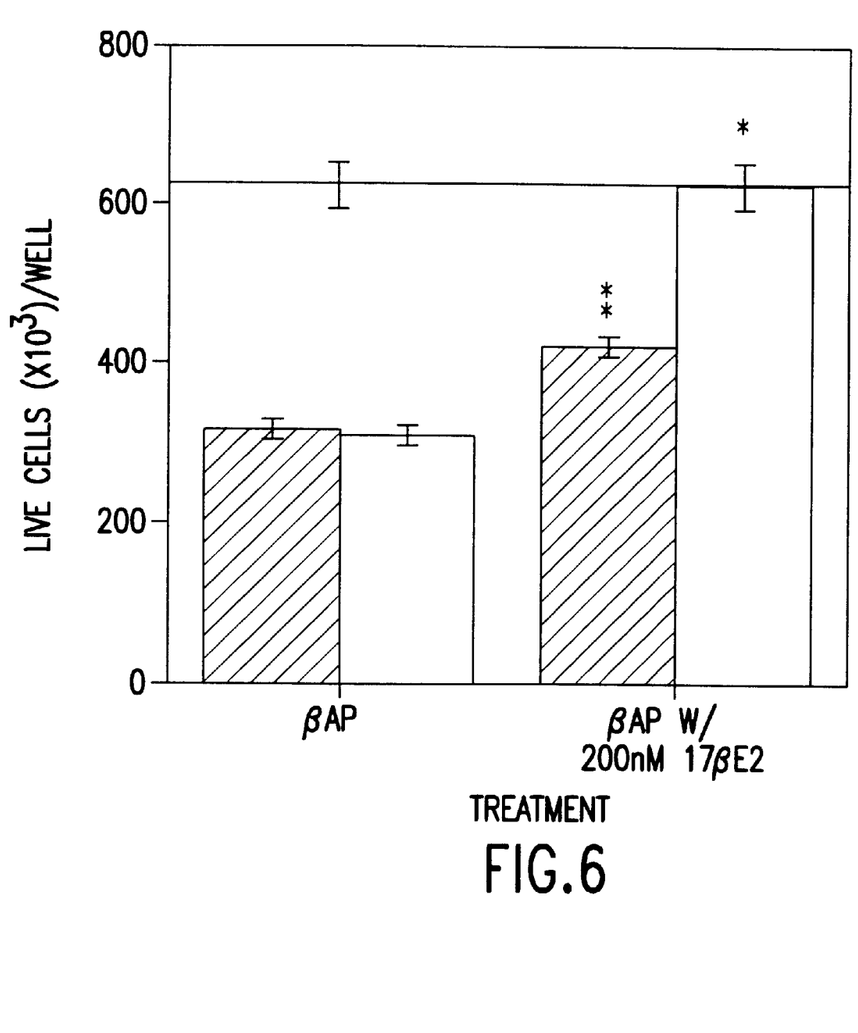
FIG. 6 shows the effects of 17β-estradiol in the presence and absence of GSH on the neurotoxicity induced by βAP 1–40 in HT22 cells. □ indicates the presence of GSH and ■ indicates the absence of GSH. The line represents the value of the control group (no βAP 1–40). The data are presented as the mean±SEM for 4 wells per group. *=p<0.05 versus the βAP 1–40 alone group **=p<0.05 versus both the βAP 1–40 alone group and the control (no βAP 1–40) group.

As shown in FIG. 1, the cytoprotective effect of 17β-estradiol and glutathione on human neuronal cells (SK-N-SH) was significantly greater than the cytoprotective effect of 17β-estradiol and glutathione individually. This effect was consistently observed when the cells were incubated in different media. FIG. 2 further illustrates this effect where maximum cell protection was observed earlier and at lower concentrations of glutathione when 17β-estradiol was included in the media. A similar observation was made in FIGS. 3 and 4 when glutathione was added in a constant amount to increasing concentrations of 17β-estradiol in human neuron cells and also rat primary cortical neurons. A marked synergistic effect was also noted when an estrogen having insubstantial sex activity was used (α-estradiol). (FIG. 5). FIG. 5 further shows increases in neuroprotective effect of 100–600 fold for three different estrogen compounds. We have found that estratrienes exhibit approximately 1000–5000 fold enhancement in their cytoprotective effect when administered with the anti-oxidant, glutathione. In embodiments of the invention, the enhancement observed with different combinations of agents falls within the range of 100 fold to 10,000 fold. The synergistic effect of anti-oxidant and estrogen compound was further observed in cells that lacked an estrogen receptor. FIG. 6 shows the synergistic effect of glutathione with 17β-estradiol in HT-22 cells.

The methods of assaying the cytoprotective effect described in these examples may readily be applied to identifying the extent of the synergistic effect between additional polycyclic phenolic compounds and anti-oxidants, beyond those disclosed herein. Furthermore, cells other than neuronal cells may be used according to the assays described here to demonstrate the cytoprotective effect of polycyclic phenolic compounds with anti-oxidants. These assays and applications are within the scope of the invention as embodied here.

Although the above examples describe synergy using glutathione as an anti-oxidant, other anti-oxidants may be used to obtain the observed synergistic effect. Table 1 provides a summary of the effects of 17β-estradiol together with a variety of anti-oxidants, and their combination on neuronal cells.

The applicants are under no duty or obligation to explain the mechanism by which the invention works. However, the following mechanism is suggested to explain the observed synergistic effect. It is known in the prior art that estrogen compounds are lipophilic molecules. Given the lipophilic character of estrogen, estrogen may insert into the membrane. Based upon the observation that an intact phenolic group is desirable for cytoprotection, the hydroxyl hydrogen may be donated to prevent the cascade of membrane lipid peroxidation. Additionally, the enhanced potency of estrogens may result from its ability to donate from several positions on the A ring (Jellnick and Bradlow, 1990). A relatively stable oxidized form of estradiol may result from this hydrogen ion donation. It is proposed here that for example, a glutathione peroxidase can regenerate the reduced form of estrogen. This enzyme relies on GSH as its substrate for donation of the hydrogen group back to estrogen, and thereby result in a synergy between the activity of the two molecules.

The specificity of estrogens interaction for this glutathione system is supported by two lines of evidence. First, there are no apparent interactions noted between estrogen and the other thiols tested, lipoic acid or taurine, or any other anti-oxidants, including ascorbic acid or atocopherol. It should be noted that while α-tocopherol is a powerful anti-oxidant in its own right, estrogen has been argued to be even more powerful. Second, the ability of oxidized glutathione to work in this system, argues that estrogen may be interacting with the glutathione peroxidase/reductase process.

The presence of estrogen in cell membranes is a reflection of the amounts of estrogen introduced into the blood stream. If estrogen is available, it may insert into the cell membranes of any available cell without specificity thereby providing a cell protective effect. However, as the amounts of estrogen become limiting, estrogens may predominantly located in the membranes of cells bearing estrogen receptors.

On the basis of the above mechanism, applicants assert that cell protection resulting from the synergistic effect of polycyclic phenolic compounds and anti-oxidants may occur for any of the cells of the body and is not restricted to the examples provided here. Applicants have previously demonstrated the cell protective effect of polycyclic phenolic compounds alone on neurons, glial cells, (U.S. Pat. No. 5,554,601) endothelial cells (U.S. Ser. No., 08/749,703) skeletal muscle, and erythrocytes (U.S. Ser. No. 08/782, 883). In addition, osteoblasts, smooth muscle cells including cardiac muscle cells, fibroblasts, and stem cells should all be protected by the synergistic effect of polycyclic phenolic compounds and anti-oxidants.

The Synergistic Effect is Receptor Independent.

We have shown that the observed synergistic effect does not depend on the nuclear estrogen receptor (ER). This observation may lead to new methods of designing drugs for treating abnormal cellular loss in human subjects.

The ER-independent synergistic effect was confirmed by experiments using the murine neuronal cell line (HT-22), which lacks a functional estrogen receptor (FIGS. 5 and 6). When these cells were exposed to the neurotoxic βAP 25–35 about 50–60 % of the cells were killed. Concurrent treatment with either of three estratrienes, β-estradiol, α-estradiol or estratriene-3-ol, resulted in dose-dependent neuroprotection. (FIG. 5). The presence of specific $^3$H estradiol binding to both nuclear extracts and whole cell preparations was determined by assays described by Miranda et al. J. Neurobiol 31, (1996), 77–87; and Nakao et al. Atherosclerosis 38 (1981) 75–80). Binding of estradiol to HT22 cells was compared with binding to MCF-7 cells carrying the ER receptor. HT-22 cells did not demonstrate specific binding in either assay with only 6±3.93 fmol specific binding per million cells compared to 56±6.5 for the ER positive MCF-7 cell line in the whole cell preparation and 0.05 fmol per million cells compared to 35.21 for the MCF-7 cells in the crude nuclear pellet. The protection conferred by physiological doses of estrogens on these cells confirms that a major portion of the protective effects of estrogens is independent of the ER.

It should be noted that whereas β-estradiol is a sex hormone and known to act through the estrogen receptor, α-estradiol or estratriene-3-ol are generally believed to be biologically inactive according to the art. These compounds are all examples of polycyclic phenolic compounds. The invention encompasses the use of any of the class of polycyclic phenolic compounds independent of their ability to bind the estrogen receptor.

We tested estradiol conjugated to bovine serum albumin (BSA) to determine if estradiol could protect HT-22 cells from β-AP (25–35) if the estrogen was restricted to the extracellular environment. Immobilization of the steroid by BSA conjugation (17β-estradiol-6-(carboxymethyl) oxime: BSA containing 20 μM 17β-estradiol) abolished the ability of the steroid to protect HT22 cells from βAP (25–35) toxicity in the presence of GSH (Example 2a, Table 2). This is consistent with similar observations with SK-N-SH cells. Collectively, these data suggest that desirability of free interaction of the estratrienes with the cell membrane or the intracellular space so as to exert their neuroprotective effects.

The dose of GSH used in these studies had no effect on β-AP (25–35) induced toxicity by itself inasmuch as β-AP (25–35) caused a 54±4% and a 55±3% decrease in cell viability in the absence and presence of 3.25 pM GSH, respectively. However, a GSH dose of 325 μM showed significant protection from β-AP toxicity in SK-N-SH neuroblastoma cells (FIG. 2). Further, exposure of HT-22 cells to 3.25 μM GSH alone, 200 nM 17β-estradiol alone, or both in combination did not cause an increase in cell number in the absence of an insult (FIG. 6) indicating that the increase in cell number is due to protection and not to a mitogenic effect of the compounds.

Applications of the Observed Synergistic Effect Between Polycyclic Phenolic Compounds and Anti-oxidants.

A pharmaceutical preparation including a polycyclic phenolic compound and an anti-oxidant may be used for treating subjects suffering from trauma, chronic degenerative diseases or acute disease such as induced by an ischemic attack. Examples include Alzheimer's disease, Parkinson's disease, stroke, ischemia, heart attack or angioplasty, or brain or spinal cord trauma, hypoglycemia, anoxia, burns or surgeries that result in the loss of nutrient flow to the tissues.

Embodiments of the invention may further be applied to the procedure of tissue transplantation, prior, during or after removal or reperfusion of cells, tissues or organs or during storage of the cells, tissues or organs and is applicable to any of the cells in the body. The following examples are presented are not intended to be limiting but nonetheless effectively illustrate the novel biological effect of the invention.

Example 1

The Synergistic Effect of an Anti-oxidant with a Polycyclic Phenolic Compound using SK-N-SH Human Neuronal Cells Glutathione was selected as an anti-oxidant and 17β-estradiol was selected as the polycyclic compound. The assay utilized the human neuroblastoma cells SK-N-SH. The cells were treated with toxins, known to cause cell death, found in amyloid plaque-β-AP(1–40) and β-AP (25–35). The numbers following "AP" correspond to the size and type of protein fragment identified by amino acid residue number.

Materials: Lyophilized βAP 25–35 (1 mg) (Bachem, Torrance, Calif.) was initially dissolved in 200 μl ddH20 and with the addition of 800 μl of PBS, rapid aggregation was observed. 17β-estradiol (17β-estradiol, Steraloids, Wilton, N.H.), was initially dissolved at 10 mg/ml in absolute ethanol (Fisher Scientific Inc., Orlando, Fla.) and diluted in cell culture media to obtain the necessary concentrations. α-tocopherol acetate was initially dissolved in 200 μl absolute ethanol and diluted in cell culture media to the appropriate concentrations. Lipoic acid (thiotic acid), taurine (2-aminoethanoic acid), and ascorbic acid were initially dissolved in cell culture media and used at the concentrations indicated. Unless otherwise noted, materials were obtained from Sigma Chemical Corp SK-N-SH Neuroblastoma Cell Culture: SK-N-SH neuroblastoma cells were obtained from American Type Tissue Collection (Rockville, Md.). Cell cultures were grown to confluency in RPMI-1640 media (Fisher Scientific, Inc.) supplemented with 10% charcoal/dextran-treated fetal bovine serum (FBS), (Hyclone®), Logan, Utah), 100 U/ml penicillin G and 100 mg/ml streptomycin (Sigma Chemical Corp.) in monolayers in Corning 150 cm$^2$ flasks (Fisher Scientific, Inc.) at 37° C. under 5% $CO_2$, 95% air. Media was changed three times weekly. Cells were observed with a phase contrast microscope (Nikon Diaphot-300).

(a) SK-N-SH cells used in the following experiments were in passes 4 to 12. The growth media was initially decanted and the cells were rinsed with 0.02% EDTA for 30 min at 37° C. Cells were then counted on a Neubauer hemacytometer (Fisher Scientific) and resuspended in appropriate media. Studies were initiated by plating 1×10⁶ cells per well in 24 well plates, allowing attachment in regular media and then decanting that media and replacing with the appropriate treatment after 4 h. Cells were cultured in DMEM or RPMI-1640 without GSH (reduced), supplemented with 10% FBS and antibiotics, with absolute ethanol as a vehicle control, or supplemented with the addition of βAP 25–35 (20 μM), 17β-estradiol (0.002 –200 nM ), GSH (0.0325–325 μM), α-tocopherol acetate (50 μM), ascorbic acid (100 μM), lipoic acid (10 μM), taurine (5 mM), or a combination as indicated. The 20 μM concentration of βAP was selected as we have shown that it is near the $LD_{50}$ for this peptide (Green et al., 1996). Selection of anti-oxidant concentrations were made on the basis of preliminary dose-response evaluations used to identify the concentration at which neuroprotection was not obtained.

SK-N-SH cell viability was determined utilizing the trypan blue exclusion method (Black and Berenbaum, 1964; Tennant, 1964). After 72 h of incubation, treatment media was decanted and cells were lifted by incubating with 0.2 ml 0.02% EDTA for 30 min at 37° C. Cells were suspended by repeated pipetting. One-hundred μl aliquots from each cell suspension were incubated with 100 μl aliquots of 0.4 % trypan blue stain for 5 min at room temperature. All suspensions were counted on a Neubauer hemacytometer within 10 min of addition of trypan blue stain. Two independent counts of live and dead cells were made for each aliquot.

were treated simultaneously with Aβ 25–35: (20 μM), a series of concentrations of glutathione ranging from 0–325 μM and a single dose concentration of 17β-estradiol (2 nM). After 72 hours incubation, live cells were determined with Trypan Blue exclusion. As shown in FIG. 2, in the absence of 17β-estradiol, glutathione had an $ED_{50}$ of 32.5 μM and showed little neuroprotective effect at 3.25 μM. In contrast, in the presence of 17β-estradiol, the $ED_{50}$ was shown to be 0.325 μM providing 1000 fold greater neuroprotectivity then with glutathione alone.

Figure 3:
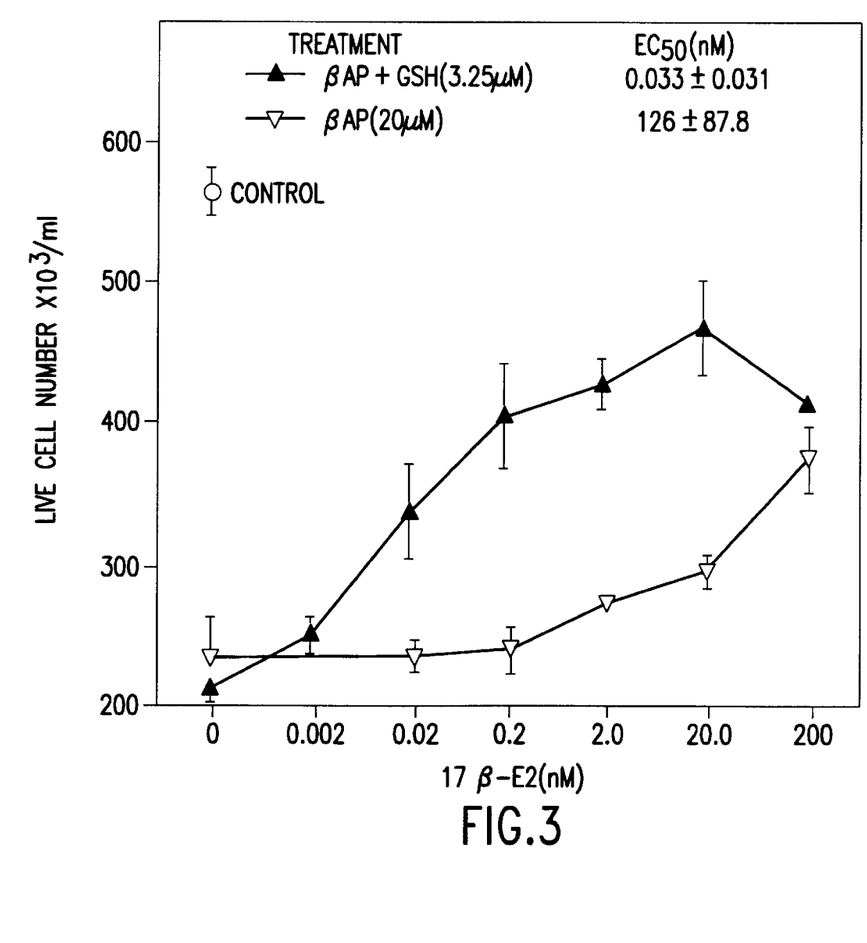
FIG. 3 shows the effect of GSH and 17β-estradiol on live SK-N-SH cell number subjected to a challenge with βAP 25–35 (20 μM) at varying concentrations of 17β-estradiol in the presence of 3.25 μM GSH (filled triangles) compared with effects in cells treated with 17β-estradiol in the absence of GSH (open triangles). Depicted are the mean values±SEM for 4 wells per group. The effect of GSH on the response to 17β-estradiol was highly significant (F=44.33; p<0.001). A comparison of the $EC_{50}$ values for the different dose response curves using the Mann-Whitney Rank Sum Test showed a p<0.057 where the $EC_{50}$ for βAP 25–35+ GSH(3.25 μM) was 0.33±0.031 and for βAP 25–35 (20 μM) was 126±87.8.

(c) Using the assay described above, SK-N-SH cells were treated with Aβ 25–35(20 μM) a single concentration of glutathione (3.25 μM.) and a variable concentrations of 17β-estradiol in the range of 0–200 nM. After 72 hours incubation, the cells were stained with Trypan Blue. Neuroprotection was observed at concentrations of 200 nM 17β-estradiol in the absence of glutathione with an $ED_{50}$ of 100 nM. In the presence of glutathione and 17β-estradiol, the $ED_{50}$ was 0.02 nM. Thus the neuroprotective potency of 17β-estradiol reaches 5000 fold in the presence of glutathione compared to in the absence of glutathione. (FIG. 3).

Neuroprotection provided by 17β-estradiol alone was 628-fold less than in the presence of GSH. Following βAP (1–40) treatment of cells, a 200 nM 17β-estradiol dose provided 99.9% and 35.6% protection in the presence and absence of GSH, respectively (FIG. 1). α-17-E2 and E-3-ol estrogens both behaved similarly to with an $ED_{50}$ of 6 nM and 14 nM, respectively, in the presence of GSH and $ED_{50}$ of 1014 nM and 3683 nM, respectively, in the absence of GSH.

TABLE 1

Effects of 17 β-estradiol (17β-estradiol), a variety of anti-oxidants, and their combination on the βAP 25–35 induced toxicity in SK-N-SH live cell number. The numbers indicate live cell numbers

|  | Ascorbic Acid (100 μM) | Tocopherol (50 μM) | Taurine (5 mM) | Lipoic Acid (10 μM) | GSH (3.25 μM) | GSSG (1.5 μM) |
|---|---|---|---|---|---|---|
| Control | 365 ± 9 | 641 ± 25 | 628 ± 13 | 628 ± 13 | 657 ± 30.0 | 657 ± 30 |
| βAP | 118 ± 9* | 366 ± 24* | 408 ± 10* | 408 ± 10* | 331 ± 17* | 331 ± 17* |
| βAP + βE2 | 144 ± 9 | 407 ± 21 | 394 ± 3 | 393 ± 3 | 357 ± 19 | 357 ± 19 |
| βAP + TRT | 124 ± 6* | 448 ± 12* | 402 ± 9* | 406 ± 7* | 369 ± 7* | 350 ± 29* |
| βAP + βE2 + TRT | 188 ± 11* | 456 ± 14* | 439 ± 11* | 416 ± 10* | 534 ± 16* | 513 ± 7* |

*–p<0.05 versus vehicle treated controls
x=p<0.05 versus βAP treated controls
TRT=treatment with anti-oxidant indicated
Statistics: The significant treatment effects on cell viability were determined using ANOVA followed by Scheffe's post hoc test, with significance determined at p<0.05. For dose-response evaluations, $EC_{50}$ values were calculated by randomly assigning cell counts at the indicated doses to generate 3–5 lines per treatment and determining the average value for those lines. Mann-Whitney Rank Sum non-parametric analysis were used on $EC_{50}$ values because the variances for the standard deviation were not equivalent. Comparisons between dose response relationships were calculated using two-way ANOVA to determine the significance of GSH or 17β-estradiol presence or absence.

(b) Human SK-N-SH were back cultured into 96 well plates in an RPMI media lacking glutathione. Four hours later, one group of plates of cells were treated simultaneously with the neurotoxic β-amyloid protein βAP 25–35: (20 μM) and a series of concentrations of glutathione ranging from 0–325 μM. A second group of plates of cells Example 2

The Synergistic Neuroprotective Effect of an Anti-oxidant with a Polycyclic Phenolic Compound on Murine Neuronal Cells that Lack Functional Estrogen Receptors (HT-22) using an in vitro Assay.

(a) Effects of 17β-estradiol and 17β-estradiol-6-(carboxymethyl)oxime: BSA conjugate on βAP 25–35 Induced Toxicity on HT-22 cells.

Experiments were initiated by plating cells in Nunc® 24 well plate and cells were allowed to attach for 4 h before treatment. Cells were exposed to 20 μM βAP 25–35 in the presence of the indicated dose of 17β-estradiol or 17β-estradiol-BSA in RPMI media containing 3.25 μM GSH. After 48 h cells were suspended and viability determined using the trypan blue due exclusion method (Tennant J. R. (1964) Transplantation 2 (1964) 685–694. Steroids and βAP were prepared as previously described (Green et al. Neuroscience Lett. 218, (1996) 165–168). Data were analyzed by a one way Analysis of Variance and a Scheffe's post-hoc analysis was used for planned comparisons between groups. Data are presented as mean±sem for 4 wells per group. *=p<0.05 versus the βAP (20 μM) group.

TABLE 2

Effects of 17β-estradiol and 17β-estradiol-6 (carboxy-methyl) oxime:BSA Conjugate on βAP (25–35) Induced Toxicity on HT-22 Cells

| Treatment | Live Cell Number ($\times 10^3$ cells) ± SEM |
|---|---|
| Control (No βAP) | 427 ± 11* |
| βAP (20 μM) | 189 ± 11 |
| βAP + 0.2 μM β17-E2 | 324 ± 14* |
| βAP + 20 μM β17-E2:BSA | 216 ± 17 |

(b) Effects of Estratrienes in the Presence and Absence of Gluthathione on the Neurotoxicity Induced by βAP 25–35 in HT-22 cells.

Experiments were initiated by plating cells in Nunc® 24 well plate cells were allowed to attach for 4 h before treatment. Cells were exposed to 20 μM βAP in the presence of the indicated dose of 17β-estradiol or α17-E2 or E-3-ol (0–20,000 nM) either in RPMI media containing 3.25 μM GSH or RPMI media without GSH. After 48 h cells were suspended and viability determined using the trypan blue dye exclusion method (Tennant 1964). Steroids and βAP were prepared as previously described (Green et al. 1996). $ED_{50}$ values were analyzed by a two way Analysis of Variance. Differences among effects were determined by a Scheffe's post hoc analysis with a p<0.05 considered significant. The glutathione effect is significant with a p<0.001. Data are normalized to the βAP free control group as 100% protection and the βAP alone group as 0% protection. The mean±sem for 3–5 wells per group are presented in FIG. 3

(c) Effects of 17β-estradiol in the presence and absence of glutathione on the neurotoxicity induce by βAP (1–40) in HT-22 cells.

Experiments were carried out as described in Example 2(b) with the exception of βAP (1–40) was allowed to incubate for 4 days before dilution to 20 μM in the culture media. The aging of βAP is necessary to aggregate the peptide, so as to render the toxic effect on the cells (Pike et al. J.Neurosci, 13 (1993) 1676–1687). Data were presented as mean±sem for 3–4 wells per group. Data was analyzed by one way Analysis of Variance and p<0.05 was considered significant.(FIG. 5)

The results as shown in FIG. 5 and 6 demonstrate the neuroprotective effect of both GSH with β-estradiol on HT22 cells following treatment with one of two types of the neurotoxin β-AP. A synergistic interaction between neuroprotective estrogens and the protection conferred by the intracellular anti-oxidant GSH was observed. 17β-estradiol, the potent naturally occurring estrogen, protected HT-22 cells from cell death induced by the neurotoxic amyloid fragment, β-AP (25–35) fragment with an $ED_{30}$ of 5 nM and significant neuroprotection with 2 nM of the steroid and 3.25 μM GSH (FIG. 5).

Example 3

The Neuroprotective Effect of Estrogen Compounds with an Anti-oxidant on Primary Rat Cortical Neuron Cultures.

To ensure that the synergistic effect observed in Examples 1 and 2 was not due to cell origin or tumorigenicity, we performed similar experiments in rat primary cortical neurons. Primary Rat Cortical Culture: Primary neuronal cultures were prepared according to the method used by Chandler et al. Alcoholism: Clinical and Experimental Research, 17 (1993) 54–60.

Treatments were made directly to primary cultures on culture day 10, maintaining a constant volume added regardless of treatment as follows: Controls: absolute ethanol and PBS, samples: βAP 25–35 (10 μM), 17β-estradiol (0.02 nM–2 μM), GSH (3.25 μM), or combinations as indicated. Once treatments were added, primary cultures were incubated for an additional 24 h and viability determined using the LIVE/DEAD® viability/cytotoxicity kit (Molecular Probes, Eugene, Oreg.) according to manufacturer's instructions. Live cells are distinguished by the presence of intracellular esterase activity which cleaves the calcein AM dye, producing a bright green fluorescence when excited. Ethidium homodimer enters cells with damaged membranes, and upon binding to nucleic acids, produces a red fluorescence. Both dyes are excited at 485 nm, and cultures plates were viewed with a fluorescent microscope (Nikon Diaphot-300). Three random fields were photographed, and the average number of live cells per field was determined by counting the number of bright green cells. Again, the ability of estradiol was evaluated in the presence and absence of GSH (3.25 μm) (FIG. x). The addition of βAP 25–35 (10 μM) to primary cortical neurons resulted in a 39% to 40% reduction in the average number of viable cells per field in the absence and presence of GSH, respectively (FIG. 4). When increasing doses of 17β-estradiol were evaluated with βAP 25–35, the 200 μM dose of 17β-estradiol was the lowest dose found to be protective, which is in full agreement with our SK-N-SH cell line studies (FIGS. 1–3). With the addition of GSH (3.25 μM) to 17β-estradiol, all doses of 17β-estradiol of 2 μM or higher were neuroprotective (FIG. 4). Evaluation of $EC_{50}$ values demonstrate similar changes in potency, from 68.1±79 μM in the absence of GSH, to 4.3±5.9 μM in the presence of GSH. Likewise, evaluation of the effect of GSH on the neuroprotective effect of 17β-estradiol in rat primary cultures using two-way ANOVA demonstrated a significant effect (F:8.53; p<0.005).

We claim:

1. A method for conferring cytoprotection on a population of cells comprising:
    (a) providing a polycyclic phenol compound, and an anti-oxidant compound; and
    (b) administering the polycyclic phenol compound and the anti-oxidant compound to the population of cells at an effective dose so as to confer cytoprotection such that the combined cytoprotective effect of the polycyclic phenolic compound and the anti-oxidant compound is greater than the additive effect of each compound administered separately under otherwise similar conditions.

2. A method according to claim 1, wherein the polycyclic phenolic compound is an estrogen compound.

3. A method according to claim 1, wherein the anti-oxidant is selected from the group consisting of a thiol, a phenol, a spin trapping agent, an aromatic amine, a carotenoid, a flavonoid, a selenium, an aminosteroid and an ubiquinone.

4. A method according to claim 2, wherein the anti-oxidant is selected from the group consisting of a thiol, a phenol, a spin trapping agent, an aromatic amine, a carotenoid, a flavonoid, a selenium, an aminosteroids and an ubiquinones.

5. A method according to claim 1, wherein the anti-oxidant is a glutathione.

6. A method according to claim 2, wherein the anti-oxidant is a glutathione.

7. A method according to claim 2, wherein the estrogen has insubstantial sex activity.

8. A method according to claim 2, wherein the estrogen compound is an estratriene.

9. A method according to claim 1, wherein the synergistic effect is in the range of of 100–10,000 fold.

10. A method according to claim 1, wherein the population of cells are neuronal cells.

11. A method according to claim 1, wherein the cells are cardiovascular cells.

12. A method according to claim 1, wherein the cells are cerebrovascular cells.

13. A method according to claim 1, wherein the cells are body cells that have been exposed to an ischemic event.

14. A method of conferring cytoprotection on a population of cells in a subject, comprising:
(a) providing a combination therapeutic dose containing an anti-oxidant and a polycyclic phenolic compound in a pharmaceutical formulation;
(b) administering the formulation in an effective dose to the population of cells such that the cytoprotective effect of the combination in the subject is greater than the additive effect of each compound provided separately; and
(c) protecting cells in the subject that would otherwise deteriorate and die in the absence of the pharmaceutical formulation.

15. A method according to claim 14, wherein the polycyclic phenolic compound is an estrogen compound.

16. A method according to claim 14, wherein the anti-oxidant is selected from the group consisting of a thiol, a phenol, a spin trapping agent, an aromatic amine, a carotenoid, a flavonoid, a selenium, an aminosteroids and an ubiquinones.

17. A method according to claim 15, wherein the anti-oxidant is selected from the group consisting of a thiol, a phenol, a spin trapping agent, an aromatic amine, a carotenoid, a flavonoid, a selenium, an aminosteroids and an ubiquinones.

18. A method according to claim 14, wherein the anti-oxidant is a glutathione.

19. A method according to claim 15, wherein the anti-oxidant is a glutathione.

20. A method according to claim 15, wherein the estrogen has insubstantial sex activity.

21. A method according to claim 14, wherein the estrogen compound is an estratriene.

22. A method according to claim 14, wherein the synergistic effect is in the range of of 100–10,000 fold.

23. A method according to claim 14, wherein the population of cells are neuronal cells.

24. A method according to claim 14, wherein the cells are cardiovascular cells.

25. A method according to claim 14, wherein the cells are cerebrovascular cells.

26. A method according to claim 14, wherein the cells are body cells that have been exposed to an ischemic event.

* * * * *

UNITED STATES PATENT AND TRADEMARK OFFICE
CERTIFICATE OF CORRECTION

PATENT NO. : 5,972,923

DATED : October 26, 1999

INVENTOR(S) : Simpkins et al.

It is certified that error appears in the above-identified patent and that said Letters Patent is hereby corrected as shown below:

Column 13, line 8, delete "of" after --of--
Column 14, line 20, delete "of" after --of--

Signed and Sealed this

Second Day of May, 2000

Attest:

Q. TODD DICKINSON

*Attesting Officer*        *Director of Patents and Trademarks*